United States Patent
Scaggs

(10) Patent No.: US 8,848,177 B2
(45) Date of Patent: Sep. 30, 2014

(54) APPARATUS FOR FOCUS BEAM ANALYSIS OF HIGH POWER LASERS

(71) Applicant: Haas Laser Technologies, Inc., Flanders, NJ (US)

(72) Inventor: Michael J. Scaggs, Weston, FL (US)

(73) Assignee: Haas Laser Technologies, Inc., Flanders, NJ (US)

( * ) Notice: Subject to any disclaimer, the term of this patent is extended or adjusted under 35 U.S.C. 154(b) by 0 days.

(21) Appl. No.: 14/263,382

(22) Filed: Apr. 28, 2014

(65) Prior Publication Data

US 2014/0233021 A1    Aug. 21, 2014

Related U.S. Application Data

(62) Division of application No. 13/657,126, filed on Oct. 22, 2012, now Pat. No. 8,711,343.

(51) Int. Cl.
*G01J 1/00* (2006.01)
*G02B 3/08* (2006.01)
*G01J 1/42* (2006.01)

(52) U.S. Cl.
CPC .................. *G01J 1/4257* (2013.01)
USPC .......... 356/121; 356/122; 356/125; 356/5.05; 359/741; 359/641

(58) Field of Classification Search
USPC .............. 356/121, 122, 125, 5.05; 250/201.1; 359/642, 641, 708, 741
See application file for complete search history.

(56) References Cited

U.S. PATENT DOCUMENTS

| | | | | |
|---|---|---|---|---|
| 5,064,284 A | * | 11/1991 | Johnston et al. | 356/121 |
| 5,069,527 A | * | 12/1991 | Johnston et al. | 359/823 |
| 5,078,491 A | * | 1/1992 | Johnston, Jr. | 356/121 |
| 5,100,231 A | * | 3/1992 | Sasnett et al. | 356/121 |
| 5,214,485 A | * | 5/1993 | Sasnett et al. | 356/121 |
| 5,267,012 A | * | 11/1993 | Sasnett et al. | 356/121 |
| 5,459,565 A | * | 10/1995 | Aharon | 356/121 |
| 5,557,630 A | | 9/1996 | Scaggs | 372/95 |
| 5,946,141 A | * | 8/1999 | Harrigan | 359/642 |
| 5,956,302 A | * | 9/1999 | Maeda et al. | 369/44.23 |
| 5,991,016 A | * | 11/1999 | Irie | 356/233 |
| 7,834,302 B2 | * | 11/2010 | Ripingill et al. | 250/201.1 |
| 8,144,312 B2 | * | 3/2012 | Degnan et al. | 356/5.05 |
| 8,237,922 B2 | * | 8/2012 | Scaggs | 356/121 |
| 2003/0058455 A1 | * | 3/2003 | Ebihara et al. | 356/601 |
| 2009/0059394 A1 | * | 3/2009 | Scaggs | 359/741 |
| 2011/0249256 A1 | * | 10/2011 | Scaggs | 356/121 |
| 2012/0044487 A1 | * | 2/2012 | Carron et al. | 356/301 |

* cited by examiner

*Primary Examiner* — Sang Nguyen
(74) *Attorney, Agent, or Firm* — Ronald E. Smith; Smith & Hopen, P.A.

(57) ABSTRACT

An in-line laser beam waist analyzer system includes an optical prism that picks off a portion of a second surface reflection from either a laser processing focus lens or a protective debris shield for the processing lens and directs that focused light to a pixelated detector. This provides real time monitoring of the focused laser beam while it is processing material by welding, cutting, drilling, scribing or marking, without disrupting the process.

3 Claims, 4 Drawing Sheets

APPARATUS FOR FOCUS BEAM ANALYSIS OF HIGH POWER LASERS

BACKGROUND OF THE INVENTION

1. Field of the Invention

This invention relates, generally, to focus beam analysis of high power lasers. More particularly, it relates to focus beam analysis of multi-kilowatt fiber lasers.

2. Description of the Prior Art

Conventional measurement of a laser beam waist from a focused laser beam requires the use of a measurement system including a spinning needle, a rotating aperture or slits, or movement of either a focus lens or a pixelated detector along the optical axis of the laser beam. Use of any of these known measurements systems requires interruption of the process beam.

The prior art includes no methods to provide real time, in-line measurement of a laser based optical system, i.e., all prior art systems require insertion of a measurement system and such insertion requires interruption of the process beam.

Multiple patents, such as U.S. Pat. Nos. 5,064,284, 5,069,527, 5,078,491, 5,100,231, 5,214,485, 5,267,012 and 5,459,565, disclose methods for analyzing a multimode laser beam by passing the beam through a rotating knife edge followed by translating the focal point along the optical axis to a detector.

U.S. Pat. No. 8,237,922 discloses a method for real time measurement but such method also requires disruption of the process beam.

Some laser beam analysis equipment can be placed prior to the focus lens by looking at bleed light from a turning mirror. However, that technique provides information upstream of the optic and no information downstream of the optic which is the more important point of the system, i.e., the final focus lens or debris shield.

In view of the art considered as a whole at the time the present invention was made, it was not obvious to those of ordinary skill in the art how an apparatus for focus beam analysis that does not require interruption of the process beam could be provided.

SUMMARY OF THE INVENTION

The long-standing but heretofore unfulfilled need for an apparatus that provides focus beam analysis for high power lasers is now met by a new, useful, and non-obvious invention.

The novel apparatus includes, in a first embodiment, an optical wedge prism disposed between a laser beam light source and a process focusing lens. The process focusing lens is disposed between the optical wedge prism and a workpiece. The optical wedge prism is oriented so that it offsets the laser beam from the laser beam source axis by a few degrees. The process focusing lens is tilted so that it is normal to the offset laser beam, thereby compensating for the few degrees of offset caused by the optical wedge prism.

A second or exit surface of the process focusing lens reflects one to five percent (1-5%) of the laser beam back towards the laser beam source. The reflected percentage of the laser beam is incident upon a second or exit surface of the optical wedge prism.

A pixelated detector is disposed in light-receiving alignment with the second surface of the optical wedge prism and measures the reflected percentage of the laser beam.

The second surface of the process focusing lens reflects less than one percent to five percent (<1-5%) of the laser beam back towards the laser beam source so that this small percentage of laser beam light reverses its original path through the process focusing lens to the workpiece such that the lens power is the equivalent of two process focusing lenses. One hundred percent (100%) of the original laser light diminishes as the number of optical elements between the laser and the process increases. Optical surface losses per optical element fall within a range of less than one percent up to about five percent (<1 to 5%). When this optical surface loss per element is multiplied by the number of optical elements in the system, the workpiece sees about ninety-five to ninety-nine percent (95 to 99%) of the original power.

The preferred process focusing lens is a plano-convex lens so that a first pass of the laser beam through the process focusing lens is a pass through a plano-convex lens. Back-reflected light from the plano surface causes the laser beam to travel in a reverse direction through the process focusing lens as if the process focusing lens was formed of two plano-convex lenses placed back to back.

However, the process focusing lens is not limited to a plano-convex lens. The process focusing lens could also be a bi-convex lens, a meniscus lens, an aspheric lens, a singlet, a doublet, a triplet, or any other multi-element lens. A lens with ten (10) elements, for example, can be reduced mathematically to a single, thick lens. Any positive focus lens or lens element can satisfy the requirements of a processing focus lens.

In all embodiments, whatever the last optical element may be, the light reflected back by the second or exit surface of that last element is measured with the pixelated detector. The last surface could be plano, convex or concave—it doesn't matter as long as the pixelated detector is positioned at the focal point created by the back reflected lens system assembled in accordance with this disclosure.

In the first embodiment, the laser beam is first incident on the convex surface of the plano-convex lens and the light becomes focused as it travels through the process focusing lens. The laser beam is then incident on the plano surface of the plano-convex lens and reflects back, acquiring more focus and traveling through the process focusing lens again.

The convex surface of the plano-convex lens is a concave surface to back-reflected light. The back-reflected light therefore passes through the equivalent of a bi-convex lens which is equivalent to two plano-convex lenses placed plano to plano.

The back-reflected light is incident upon the second surface of the wedge prism which directs less than one percent to five percent (<1 to 5%) of the laser beam to a pixelated detector that monitors the focal properties of the light.

The preferred pixelated detector is a beam waist analyzer camera that provides a laser system's M-squared, beam waist diameter, focal position, astigmatism, beam divergence and Rayleigh length within a frame rate of the pixelated detector, said frame rate being less than five hundred milliseconds.

A negative power lens is positioned between the optical wedge prism and the pixelated detector to extend the effective focal length of the beam entering the pixelated detector to the same value as the process focusing lens.

The optical wedge prism and the process focusing lens are preferably coated with a suitable antireflection coating to minimize reflection losses of the laser beam. The degree of antireflection coating depends upon factors such as acceptable power loss at the target and the level of light needed at the pixelated detector. If the signal level at the pixelated detector is too low, the antireflection coating can be decreased to provide more signal to the detector with minimal effect to the laser process. In high power laser applications, it is generally desired that each optical surface has a reflectivity of less than one-half of one percent (<0.5%).

In an optical system with five (5) transmissive optical elements, this amounts to reflection loses of about five percent (5%) and therefore only ninety-five percent (95%) of the light reaches the work surface. With only one-half of one percent (0.5%) of one-half of one percent (0.5%) of light reaching the pixelated detector, changing one surface to one percent (1%) reflectivity would provide sufficient signal to the detector but would reduce the total power at the work piece to ninety-four and one-half percent (94.5%), which represents a negligible loss.

A debris shield may be positioned between the process focusing lens and the workpiece to protect the process focusing lens from processing splatter and debris from the workpiece. The debris shield thus becomes the element nearest the workpiece and the back-reflection from the entrance and exit surface of the debris shield is reflected back to the pixelated detector.

A debris shield is an optical window and every optical window includes some optical wedge. The amount of the optical wedge is typically in the three to five arcminutes (3-5') range. Reflections of both the first and second surface of the debris shield will be reflected back towards the pixelated detector. Given that the debris shield has an optical wedge, and a certain thickness, the spots focused back at the detector will be separated by the wedge angle and one of the two spots will be out of focus due to the thickness of the debris shield, i.e., one reflection travels further than the other. The surface of interest will be the second surface or exit surface of the debris shield and it would be this spot that is brought into focus at the pixelated detector.

In a second embodiment, a dove prism treated with an antireflection coating and having an entry surface and an exit surface is positioned between a laser beam light source and a process focusing lens. A first pixelated detector adapted to measure a raw laser beam diameter is positioned to receive light reflected from the entry surface.

Most of the laser beam light travels through the dove prism and the focus processing lens and impinges upon a workpiece for cutting, drilling, scribing or marking a material.

The laser beam light that is reflected from a second surface of the process processing lens is reflected back towards the laser beam source. This back-reflected light is focused at about one-half the focal length of the process focusing lens because the light travels through the process focusing lens twice and is then reflected to a second pixelated detector via the exit surface of the dove prism.

The dove prism permits on axis processing in applications where a slight angle to prevent back-reflections to the laser beam source is not desired. Back-reflection isolation in such applications is required, such isolation being attained through the use of polarizers and a Faraday rotator.

In this second embodiment, a debris shield may be positioned between the process focusing lens and the workpiece as in the first embodiment for protecting the processing focus lens from processing splatter and debris from said workpiece. Light reflected from the debris shield is focused on the second pixelated detector, thereby enabling early indication of a dirty or contaminated debris shield and avoiding the need for periodic examination of the debris shield.

In a third embodiment, a pair of matched Risley or wedge prisms, each of which has a first and second surface, is disposed in light-collecting relation to laser beam light from a laser beam light source having an optical axis. The pair of matched Risley prisms includes a first prism and a second prism, the first prism being closer to the source of laser beam light than the second prism. A process focusing lens is disposed between the pair of matched Risley prisms and a workpiece.

The first and second prisms are arranged so that their respective angles are one hundred eighty degrees (180°) out of phase so that there is no angular deviation from the optical axis and so that light reflected from respective first surfaces of the first and second prisms does not interfere with light reflected from respective second surfaces of the first and second prisms.

A first pixelated detector is disposed radially outwardly of the first surface of the first prism in light-receiving relation thereto. Back-reflected light from the focus processing lens is focused on the first pixelated detector and enables a raw laser beam to be reflected to said first pixelated detector.

A second pixelated detector is disposed radially outwardly of the second surface of the second prism in light-receiving relation thereto.

If the process focusing lens is the last optic in the apparatus that is upstream of the workpiece, then light reflected back from the process focusing lens towards the exit surface of the second prism is reflected to the second pixelated detector. This enables early indication of a dirty or contaminated process focusing lens and avoids the need for periodic examination of the debris shield.

A debris shield disposed between the process focusing lens and the workpiece may be provided for protecting the process focusing lens from processing splatter and debris from the workpiece. Light reflected from the debris shield is reflected from the second surface of the second prism and is thereafter focused on the second pixelated detector, thereby enabling early indication of a dirty or contaminated debris shield and avoiding the need for periodic examination of the debris shield.

In a fourth embodiment, a dove lens having an entry surface and an exit surface is positioned between a laser beam light source and a process focusing lens. A first pixelated detector is disposed normal to the optical axis in alignment with the entry surface of the dove prism and a second pixelated detector is disposed normal to the optical axis in alignment with the exit surface of the dove prism.

A negative power lens is positioned between the exit surface and the second pixelated detector. The negative power lens changes the focus of light directed to the second pixelated detector so that the effective focal length of the back reflected lens system light is equivalent to the effective focal length of the focus processing lens.

Light back-reflecting from the second surface of the focus processing lens travels backwards through the focus processing lens, its effective focal length decreasing by nearly a factor of two.

The negative power lens changes the effective focal length back to the original focal length so that the second pixelated detector measures the focus of the apparatus at the same effective focal length.

Light back-reflected from the process focusing lends is reflected from the exit surface of the dove prism and focused on the second pixelated detector, thereby enabling early indication of a dirty or contaminated process focusing lens and avoiding the need for periodic examination of the debris shield.

A debris shield may be provided for protecting the processing focus lens of this fourth embodiment from processing splatter and debris from the workpiece.

Light reflected from the debris shield is then reflected from the exit surface of the dove prism and focused on the second pixelated detector, thereby enabling early indication of a dirty or contaminated debris shield and avoiding the need for periodic examination of the debris shield.

When light from the debris shield is focused on the pixelated detector, the effective focal length of this back reflected light system follows the following lens equation:

$$f = \frac{(f_1 \times f_2)}{(f_1 + f_2 - d)}$$

where $f_1=f_2$ and is the focal length of the lens the light first passes through and $f_2$ is the focal length of lens the light reflects back through and d is the distance from the principle plane of the first lens and the principle plane of the lens encountered on the back reflection. Using this same equation, it can be determined what the negative power lens should be to duplicate the effective focal length of the laser processing lens that the pixelated detector sees, thus insuring that the laser beam waist analysis system is measuring an accurate sample of the laser processing beam.

A primary object of this invention is to measure a laser system's M-squared value, beam waist diameter, focal position, astigmatism and Rayleigh length while simultaneously processing a material with the laser such as cutting, drilling, scribing, marking or welding, there being no interruption of the process beam in order to make said measurements.

Another object is to have a means to detect when either a laser beam parameter is out of a suitable range for processing or to determine when an optical component is beginning to fail before a processed part is out of specification.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 1:
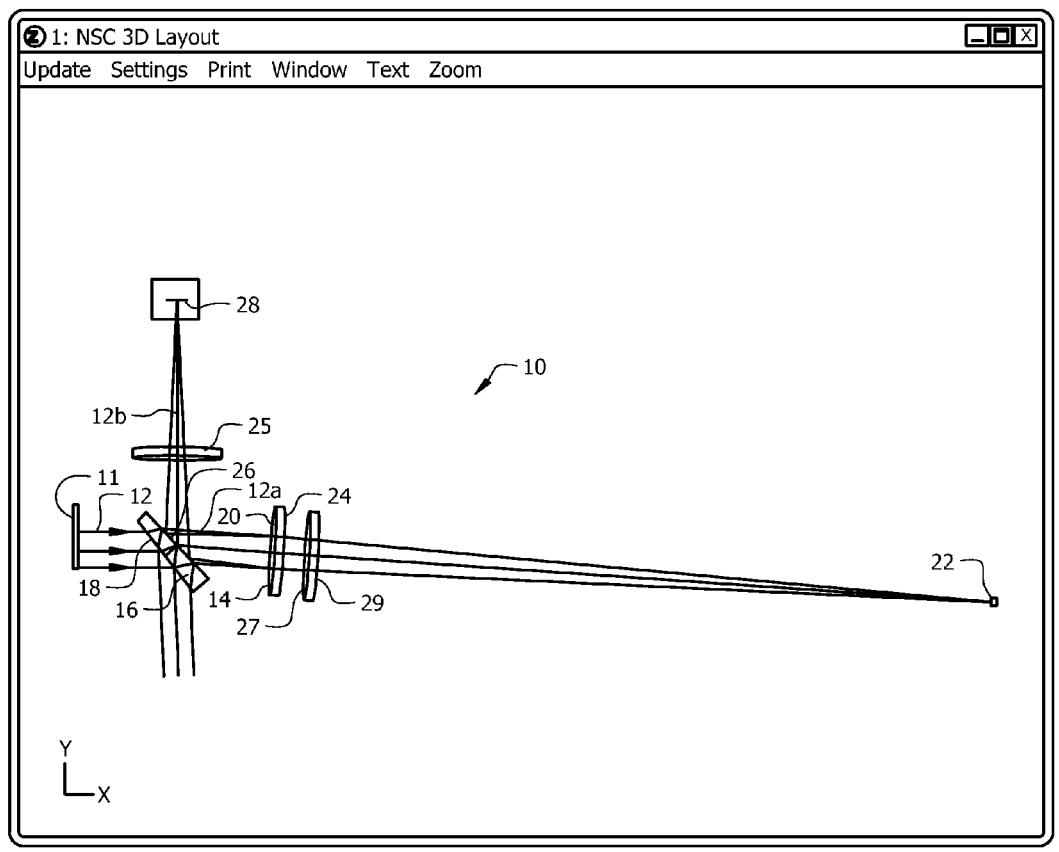
FIG. 1 is a diagrammatic disclosure of a first embodiment of the invention.

FIG. 1 depicts an illustrative embodiment of the novel structure which is denoted as a whole by the reference numeral 10.

Novel apparatus 10 enables measurement of a complete optical system incorporating a laser during laser operation without interfering with the process beam and provides real time monitoring of the focused laser beam.

The novel in-line beam waist analysis system provides the beam waist diameter, optical system M-squared value, focal length position, astigmatism, divergence and Rayleigh length concurrent to a laser processing a material/workpiece, whether it be cutting, drilling, welding, marking or scribing said workpiece.

The novel apparatus provides detailed information about how the system is performing optically from the laser through the optical elements and how it is focused at the workpiece. This makes possible a new level of quality control by providing real-time beam waist analysis to which upper and lower limits can be set to control the performance of a system while it is processing materials. The novel apparatus also warns of laser, alignment or optical element problems, thereby reducing material scrap.

FIG. 1 depicts a preferred embodiment of the invention, denoted as a whole by the reference numeral 10. Laser beam 12 generated by laser 11 is directed to process focusing lens 14. Optical wedge prism 16 coated with a suitable antireflection coating 18 is positioned between laser 11 and process focusing lens 14.

Optical wedge prism 16 directs laser beam 12 off axis a few degrees as indicated in FIG. 1. This off axis displacement, denoted 12a, is useful for welding systems where back reflections are harmful to the laser and other sensitive optics within the laser system. Process focusing lens 14 is tilted so that it is normal to prism refractive laser beam 12a to compensate for the off axis tilt.

Process focusing lens 14 is also antireflection coated as at 20 to minimize reflection losses of the processing laser beam. Laser beam 12 is focused by process focusing lens 14 on workpiece 22 to be processed or welded.

Second surface 24 of process focusing lens 14 reflects less than one percent to five percent (<1 to 5%) of incident laser beam 12a back towards laser 11. This small reflection then strikes second surface 26 of optical wedge prism 16 which then directs beam 12b to pixelated detector 28 to measure a small amount of light.

The second surface 24 reflection through process focusing lens 14 reverses its direction of travel such that the lens power is the equivalent of two process lenses.

For example, where process focusing lens 14 has a focal length of two hundred millimeters (200 mm), the second surface reflection from that lens results in an effective focal length of about one hundred millimeters (100 mm) since the light passes through lens 14 twice. This follows the basic thin lens equation of $$\frac{1}{f} = \frac{1}{f1} + \frac{1}{f2},$$

where f1=f2.

If process focusing lens 14 is a plano-convex lens, the first pass through said lens 14 is a pass through a plano-convex lens but the back-reflected light from the plano surface causes the light to reverse back through lens 14 as if it were two plano-convex lenses placed back to back. More particularly, light first strikes convex surface 20, begins to focus and travel the thickness of lens 14, strikes plano surface 24 and reflects back, focuses more and travels the same thickness again. Light passes through convex surface 20 which from the perspective of the light is a concave surface. The back-reflected light passes through the equivalent of a bi-convex lens which is the same as two of the plano-convex lenses placed plano-to-plano.

The back-reflected light then strikes second surface 26 of wedge prism 16 which directs a small percentage to pixelated detector 28 that monitors the focal properties of the light.

The preferred pixelated detector is a beam waist analyzer camera disclosed in U.S. Pat. No. 8,237,922 to the present inventor which patent is hereby incorporated by reference into this disclosure. This beam analyzer apparatus provides the laser system's M-squared, beam waist diameter, focal position, astigmatism, beam divergence and Rayleigh length within the frame rate of the camera which is well under five hundred milliseconds.

Negative power lens 25 is positioned between wedge prism 16 and pixelated detector 28 to extend the effective focal length of the beam entering the camera (i.e., the camera disclosed in said patent) to the same value as laser process focusing lens 14.

Debris shield 27 having exit surface 29 may be positioned between process focusing lens 14 and workpiece 22, thereby making said debris shield the last optical element in the apparatus. Debris shield 27 protects processing focus lens 14 from processing splatter and debris from workpiece 22. Light reflected from second surface 29 of debris shield 27 is focused on pixelated detector 28, thereby allowing early indication of a dirty or contaminated debris shield and avoiding the need for periodic examination of debris shield 27. Notification through such monitoring could tell the user that debris shield 27 requires cleaning or replacement.

In the absence of debris shield 27, process focusing lens 14 is the last optical element in the apparatus and light reflected from second surface 24 of process focusing lens 14 is focused on pixelated detector 28, thereby allowing early indication of a dirty or contaminated process focusing lens and avoiding the need for periodic examination of process focusing lens 14. Notification through such monitoring could tell the user that process focusing lens 14 requires cleaning or replacement.

Figure 2:
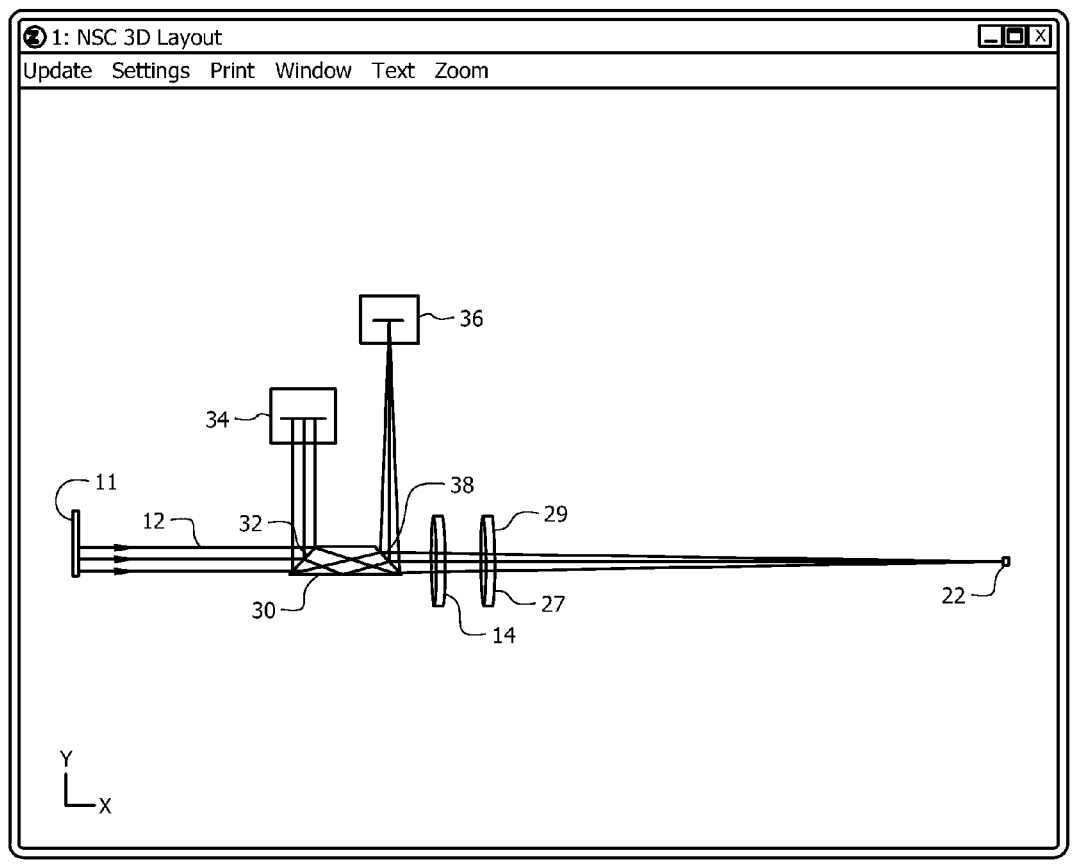
FIG. 2 is a diagrammatic disclosure of a second embodiment of the invention.

FIG. 2 depicts a second embodiment where laser beam 12 passes through antireflection coated dove prism 30. The reflection from entry surface 32 of dove prism 30 is directed to pixelated detector 34 to measure the raw laser beam diameter. The majority of the light passes through dove prism 30 and is directed through laser processing lens 14 and focused on workpiece 22 for cutting, drilling, scribing or marking a material.

The light reflected from second surface 24 of laser processing lens 14 is reflected back towards laser source 11. The back-reflected light is focused at about one-half the focal length of laser processing lens 14 since this light travels through said lens 14 twice and is then reflected to pixelated detector 36 via exit surface 38 of dove prism 30.

As in the first embodiment, debris shield 27 having exit surface 29 may be positioned between process focusing lens 14 and workpiece 22. Debris shield 27 protects processing focus lens 14 from processing splatter and debris from workpiece 22. Light reflected from second surface 29 of debris shield 27 is focused on pixelated detector 36, thereby allowing early indication of a dirty or contaminated debris shield and avoiding the need for periodic examination of debris shield 27. Notification through such monitoring could tell the user that debris shield 27 requires cleaning or replacement.

In the absence of debris shield 27, light reflected from second surface 24 of process focusing lens 14 is focused on pixelated detector 36, thereby allowing early indication of a dirty or contaminated process focusing lens and avoiding the need for periodic examination of process focusing lens 14. Notification through such monitoring could tell the user that said process focusing lens requires cleaning or replacement.

Dove prism 30 permits on axis processing where a slight angle to prevent back reflections to laser 11 is not desired. In this mode, some method of back reflection isolation is required using suitable polarizers, not shown, and a Faraday rotator, not shown, as is well known to those skilled in this art.

Figure 3:
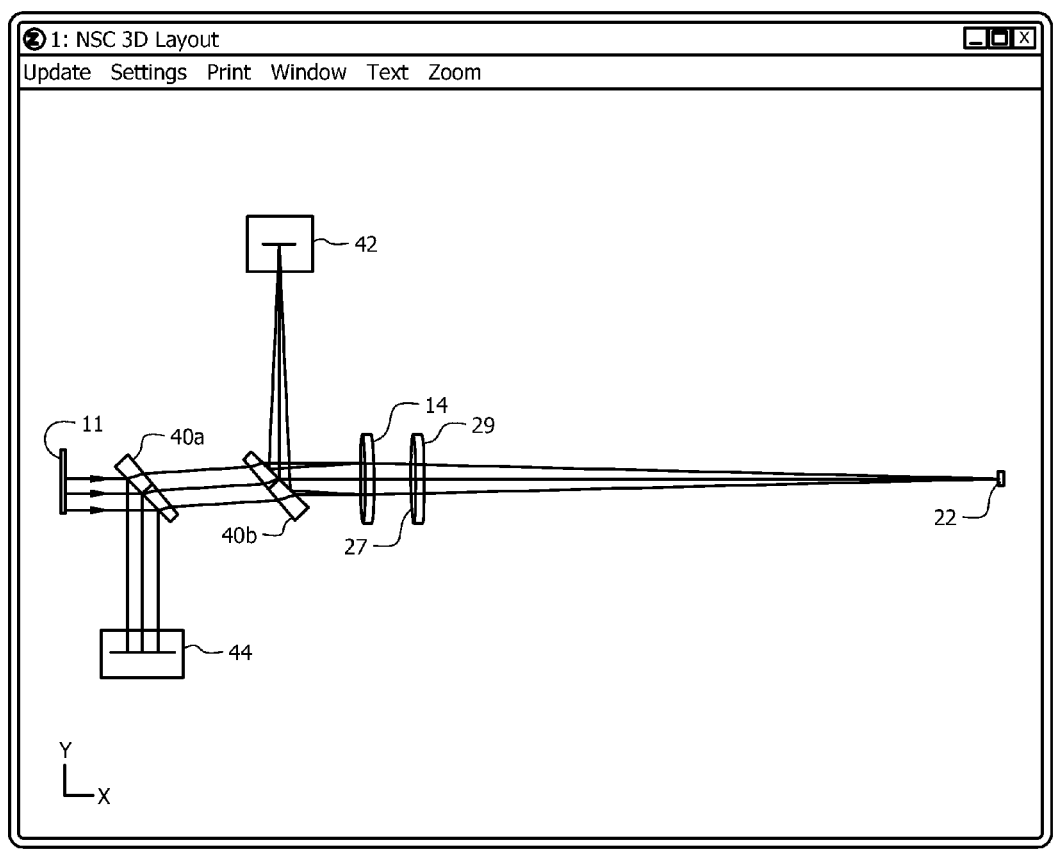
FIG. 3 is a diagrammatic disclosure of a third embodiment of the invention.

FIG. 3 depicts a third embodiment of on-axis configuration where dove prism 30 of the second embodiment is replaced with a pair of matched Risley prisms, denoted 40a and 40b. The Risley prism pair is arranged so that their angles are one hundred eighty degrees (180°) out of phase so that there is no angular deviation from the optical axis. Reflected light from the first and second surfaces will not interfere with each other. This permits the back reflected light from laser focusing lens 14 to be focused on pixelated detector 42 and enables the raw beam to be reflected to pixelated detector 44.

A "thick" optical window could replace the Risley or dove prisms. The focused spots are increasingly separated as window thickness increases. A thick optical window is less desirable than two prisms but nonetheless it could be used because a thick window is a prism that offsets light beams that travel through it.

High power fiber lasers can have powers in excess of twenty kilowatts (20 kW). If a ten kilowatt (10 kW) laser is used in a configuration as depicted in FIG. 1, for example, where each optical component has an antireflection coating of less than half of one percent (<0.5%) per surface, the amount of light reflected to the pixelated detector from the second surface of process focusing lens 14 would be one-half of one percent (0.5%) of one-half of one percent (0.5%) of ten kilowatts (10 kW) which is two hundred fifty milliwatts of power. This is a power level that essentially any conventional beam analyzing system or pixelated detector could easily accommodate with or without additional neutral density filters as required for the particular type of detector.

In the absence of a debris shield, light reflected from second surface 24 of process focusing lens 14 is focused on pixelated detector 42, thereby allowing early indication of a dirty or contaminated process focusing lens and avoiding the need for periodic examination of process focusing lens 14. Notification through such monitoring could tell the user that said process focusing lens requires cleaning or replacement.

Where debris shield 27 is provided as depicted in FIG. 3, said debris shield becomes the last optical element in the apparatus. Light reflected from second surface 29 of debris shield 27 is focused on pixelated detector 42, thereby allowing early indication of a dirty or contaminated debris shield and avoiding the need for periodic examination of said debris shield. Notification through such monitoring could tell the user that said debris shield requires cleaning or replacement.

Figure 4:
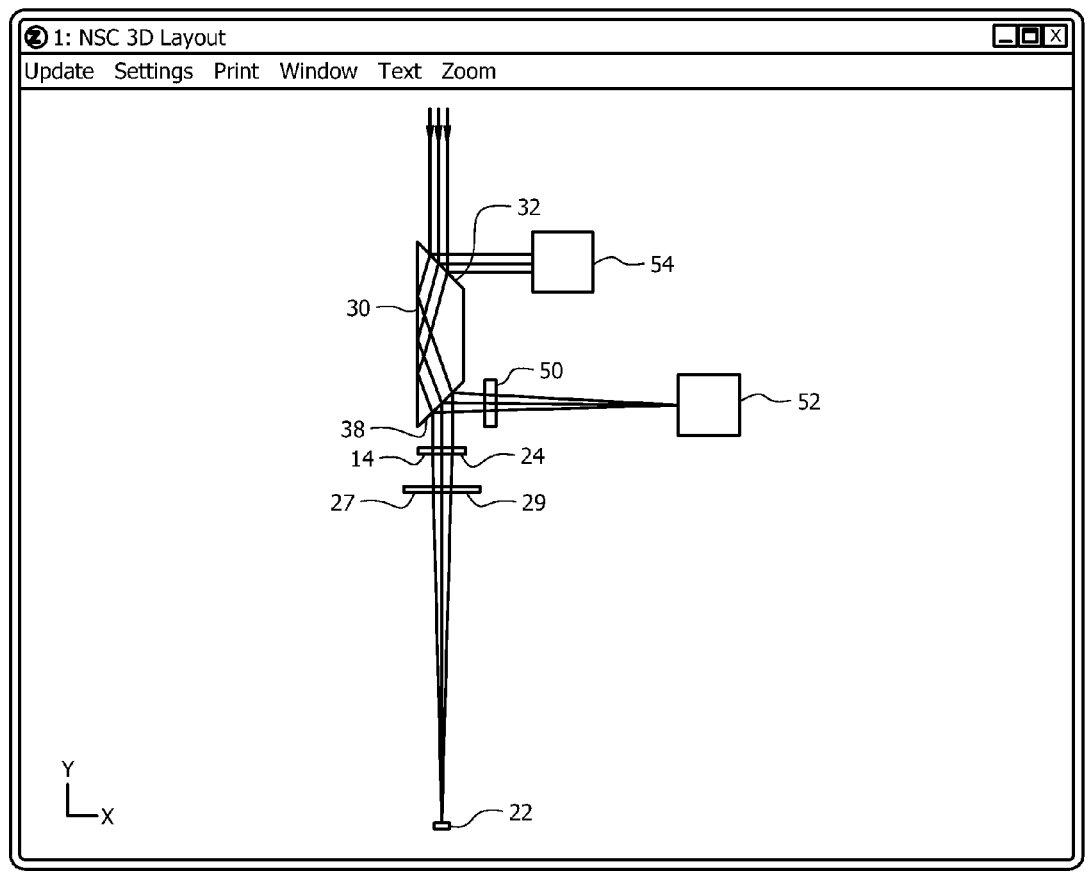
FIG. 4 is a diagrammatic disclosure of a fourth embodiment of the invention.

FIG. 4 depicts a fourth embodiment. Negative power lens 50 changes the focus of the light directed to pixelated detector 52 so that it has the same equivalent focal length as the original process focusing lens 14. Since the light back-reflecting from second surface 24 of process focusing lens 14 travels backwards through lens 14, its effective focal length decreases by nearly a factor of two as disclosed earlier. The addition of negative power lens 50 changes the effective focal length back to the original allowing pixelated detector 52 to measure the system's focus at the same effective focal length.

Pixelated detector 54 measures the raw, collimated, unfocused laser beam. The diameter of the beam at the entrance pupil of the processing lens in combination with the measured focused beam waist diameter provides the information to calculate the system's M-squared value. Moreover, pixelated detector 54 provides additional laser beam profile parameters as established by the International Organization for Standards (ISO), including all the beam parameter values outlined in the ISO standards for measuring a laser beam.

Debris shield 27 protects processing focus lens 14 from processing splatter and debris from workpiece 22. Light reflected from second surface 29 of debris shield 27 is focused on pixelated detector 52, thereby allowing early indication of a dirty or contaminated debris shield and avoiding the need for periodic examination of debris shield 27. Notification through such monitoring could tell the user that debris shield 27 requires cleaning or replacement.

In the absence of debris shield 27, process focusing lens 14 is the last optical element in the novel apparatus. Light reflected from second surface 24 of process focusing lends 14 is focused on pixelated detector 52, thereby allowing early indication of a dirty or contaminated process focusing lens and avoiding the need for periodic examination of said process focusing lens. Notification through such monitoring could tell the user that process focusing lend 14 requires cleaning or replacement.

In all four embodiments of this invention, the back-reflected light from the last surface of the last optic in the system, i.e., the optic closest to workpiece 22, is focused onto a pixelated detector in order to monitor the amount of contamination accumulating thereon as work is performed on said workpiece.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An apparatus for focus beam analysis of a high power laser, comprising:
   a dove prism positioned between a laser beam light source and a process focusing lens;
   said dove prism having an entry surface and an exit surface;
   said process focusing lens having an entry surface and an exit surface;
   a first pixelated detector positioned to receive light reflected from said dove prism entry surface, said first pixelated detector adapted to measure a raw laser beam diameter;
   a second pixelated detector positioned to receive light from said dove prism exit surface;
   a majority of said laser beam light passing through said dove prism, said process focusing lens, and impinging upon a workpiece;
   said laser beam light reflected from said exit surface of said process focusing lens being reflected back towards said laser beam source;
   said back-reflected light being focused at about one-half the focal length of said process focusing lens because said light travels through said process focusing lens twice and is then reflected to said second pixelated detector via said exit surface of said dove prism;
   whereby light reflected from said exit surface of said process focusing lens is focused on said second pixelated detector, thereby enabling early indication of a dirty or contaminated process focusing lens and avoiding the need for periodic examination of said process focusing lens;
   said dove prism permitting on-axis processing where a slight angle to prevent back-reflections to said laser beam source is not desired.

2. The apparatus of claim 1, further comprising:
   a debris shield having an entry surface and an exit surface for protecting said processing focus lens from processing splatter and debris from said workpiece;
   said debris shield disposed between said process focusing lens and said workpiece;
   whereby light reflected from said exit surface of said debris shield is focused on said second pixelated detector, thereby enabling early indication of a dirty or contaminated debris shield and avoiding the need for periodic examination of said debris shield.

3. The apparatus of claim 1, further comprising:
   said dove prism being antireflection coated.

* * * * *